(12) United States Patent
McConnell et al.

(10) Patent No.: US 9,128,108 B2
(45) Date of Patent: Sep. 8, 2015

(54) MEPHEDRONE DETECTION

(75) Inventors: Robert Ivan McConnell, Crumlin (IE); Elouard Benchikh, Crumlin (IE); Philip Andrew Lowry, Crumlin (IE); Stephen Peter Fitzgerald, Crumlin (IE)

(73) Assignee: Randox Laboratories Limted, Crumlin (GB)

( * ) Notice: Subject to any disclaimer, the term of this patent is extended or adjusted under 35 U.S.C. 154(b) by 195 days.

(21) Appl. No.: 13/275,649

(22) Filed: Oct. 18, 2011

(65) Prior Publication Data
US 2012/0094316 A1 Apr. 19, 2012

(30) Foreign Application Priority Data
Oct. 19, 2010 (GB) .................................. 1017597.4

(51) Int. Cl.
*G01N 33/556* (2006.01)
*C07K 14/765* (2006.01)
*C07K 14/47* (2006.01)
*C07K 16/44* (2006.01)
*G01N 33/94* (2006.01)

(52) U.S. Cl.
CPC .................................... *G01N 33/948* (2013.01)

(58) Field of Classification Search
None
See application file for complete search history.

(56) References Cited

PUBLICATIONS

A print-out "Abcam® Anti-Methcathinone antibody, ab123953" retrieved from www.google.com on Jun. 21, 2013.*
Torrance et al., "The detection of mephedrone (4-methylmethcathinone) in 4 fatalities in Scotland," Forensic Science International, 2010, vol. 202, issues 1-3, pp. e62-e63.*
Brandt, S.D., et al. "Analyses of second-generation 'legal highs' in the UK: initial findings." Drug Test Anal. Aug. 2010;2(8):377-82.
Brandt, S.D., et al. "Second generation mephedrone. The confusing case of NRG-1." BMJ. Jul. 6, 2010;341:c3564. doi: 10.1136/bmj. c3564.
Wood, D.M., et al. "Recreational use of mephedrone (4-methylmethcathinone, 4-MMC) with associated sympathomimetic toxicity." J Med Toxicol. Sep. 2010;6(3):327-30.
Meyer, M.R., et al. "Beta-keto amphetamines: studies on the metabolism of the designer drug mephedrone and toxicological detection of mephedrone, butylone, and methylone in urine using gas chromatography-mass spectrometry." Anal Bioanal Chem. Jun. 2010;397(3):1225-33. Epub Mar. 25, 2010.

* cited by examiner

*Primary Examiner* — Galina Yakovleva
(74) *Attorney, Agent, or Firm* — Kathleeen D. Rigaut; Dann, Dorfman, Herrell and Skillman P.C.

(57) ABSTRACT

The invention relates to an immunoassay method and kit for the detection and/or the determination of mephedrone, mephedrone metabolites and related compounds. The invention is underpinned by a novel antibody, derived from a novel immunogen, that is sensitive and binds to mephedrone, mephedrone metabolites and related compounds.

4 Claims, 3 Drawing Sheets

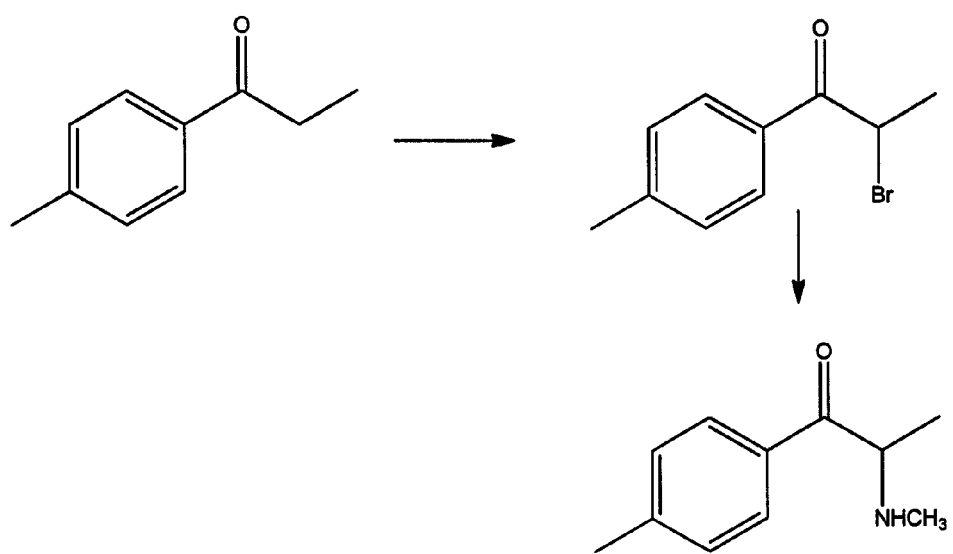
Figure 1 Mephedrone Synthetic Route

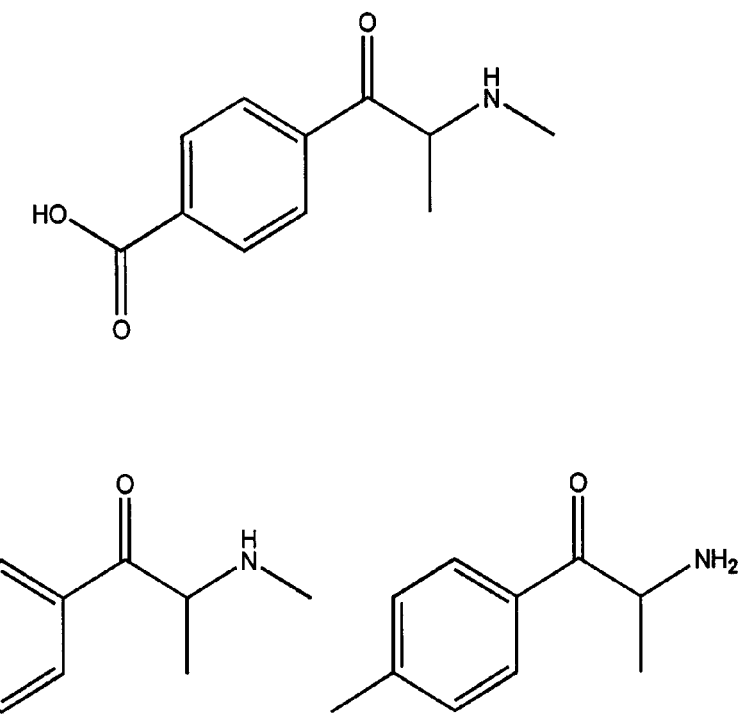
Figure 2 Metabolites of Mephedrone

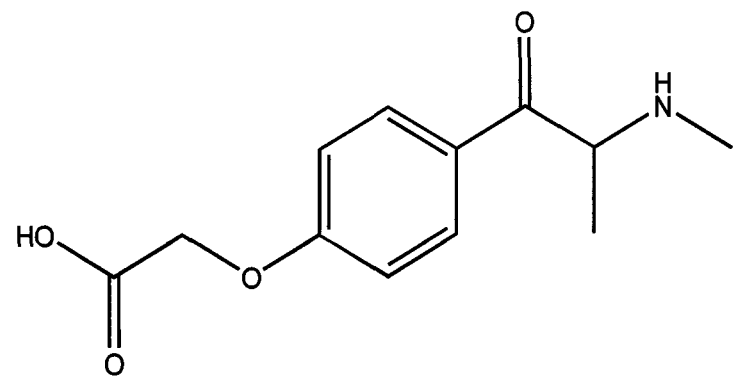
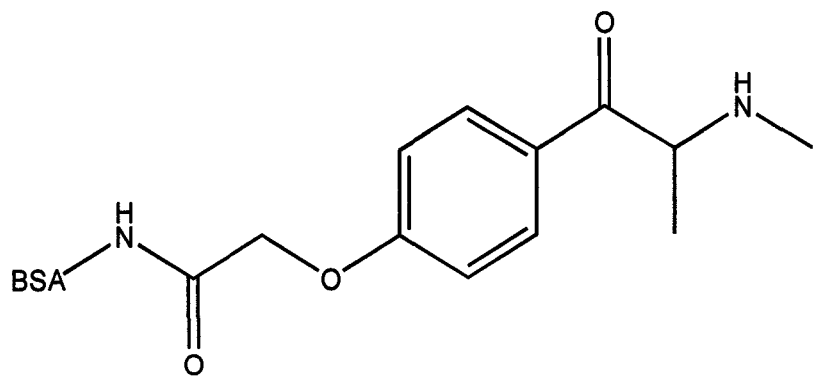
Figure 3 Hapten 1 (Top) and Immunogen 1

MEPHEDRONE DETECTION

This application claims priority to GB Patent Application No. 1017597.4 filed Oct. 19, 2010, the entire contents being incorporated herein by reference as though set forth in full.

BACKGROUND TO THE INVENTION

Mephedrone, systematic name (RS)-2-methylamino-1-(4-methylphenyl)propan-1-one, is a designer drug of the cathinone class of stimulants, implicated in a number of drug-related fatalities. It is illegal in a number of countries worldwide. Although illegal in many countries, recent studies highlighted that the accessibility and popularity of the drug is undiminished due to a re-branding approach by suppliers in which 'alternative' mephedrone products under the name of NRG-1 (Energy 1), and stated as being legal highs containing naphthylpyrovalerone, in fact contain mephedrone (Brandt et al. 2010a; Brandt et al. 2010b). The metabolism of mephedrone occurs via various combinations of oxidation of the methyl group attached to the benzene ring, N-demethylation and reduction of the keto functionality (Meyer et al. 2010). There is great potential for adverse events or abuse in individuals taking or with access to mephedrone, especially in its form as NRG-1 which by marketing as a legal high gives the impression of safety. Therefore, there is a need in clinical and forensic toxicology for its detection and/or determination using practical and inexpensive analytical methods. Analytical methods that have been used to detect and determine mephedrone and its metabolites include gas chromatography linked to mass spectrometry (GC-MS) and nuclear magnetic resonance (NMR) (Brandt et al. 2010a; Wood et al 2010; Meyer et al. 2010). A less costly and practical immunoassay has, to the inventors' knowledge never been reported for the detection or quantification of mephedrone or its metabolites.

BIBLIOGRAPHY

Brandt S. D. et al (2010a). *Drug Test. Anal.*, 2: 377-382.
Brandt S. D. et al. (2010b). *BMJ*, 341: c3564.
Wood D. M. (2010). *J. Med. Toxicol.*, 6: 327-330.
Meyer M. R. (2010). *Anal. Bioanal. Chem.*, 397: 1225-1233.

SUMMARY OF THE INVENTION

There lacks a cheap and practical test for the detection and determination of mephedrone, its metabolites and related compounds in in vitro patient samples. The current invention provides a solution to this problem by providing an antibody that binds to mephedrone, mephedrone metabolites, and compounds comprising the 2-methylamino-1-phenylpropan-1-one structure. In summary, to overcome the inadequacies associated with current analytical techniques, the inventors devised and developed an immunoassay for the detection and quantification of mephedrone, mephedrone metabolites and related compounds, based on novel antibodies. The immunoassay has many advantages over other mainstream analytical formats such as GC-MS and NMR including cost, ease of use and its amenability for manufacture in a compact, portable format for use in the field.

DRAWINGS

FIG. 1 Mephedrone synthetic route.
FIG. 2 Mephedrone metabolites.
FIG. 3 Hapten 1 and Immunogen 1.

DETAILED DESCRIPTION OF THE INVENTION

A first aspect of the invention is an immunogen of the structure

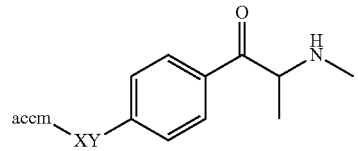

wherein, the accm is an antigenicity conferring carrier material; X is either carbonyl or amino;

Y is $-Z-(A)_n-$ in which Z is a $C_{1-5}$, substituted or unsubstituted straight chain alkylene or arylene moiety, A is O, NH, S, ester, thioester, or amide and n=0 or 1.

Preferably X is either carbonyl or amino, and Z is a $C_{1-5}$, preferably a $C_{1-3}$, unsubstituted straight chain alkylene selected from methylene, ethylene and propylene, and where n=1 and A=O, NH or S.

A preferred embodiment of the invention is an immunogen in which X=carbonyl, Z=—$CH_2$— and where n=1 and A=O. In an embodiment, before conjugation to the accm, —XY— is (COOH)—$CH_2$—O—.

The accm can be any material that makes all or part of the hapten susceptible to antibody recognition and binding. For example the accm can be a protein, a protein fragment, a synthetic polypeptide or a semi-synthetic polypeptide. Illustrative examples of useful antigenicity-conferring carrier materials are bovine serum albumin (BSA), egg ovalbumin, bovine gamma globulin, bovine thyroglobulin (BTG), keyhole limpet haemocyanin (KLH) etc. The accm is optionally selected from bovine serum albumin (BSA) and bovine thyroglobulin (BTG). In one embodiment, the immunogen is Hapten-1 coupled to BSA (FIG. 3).

The immunogens obtained are then administered to mammalian hosts to elicit production of specific antibodies, optionally polyclonal antibodies, which are then used to develop immunoassays for mephedrone, mephedrone metabolites, and compounds comprising the 2-methylamino-1-phenylpropan-1-one (methcathinone) structure, employing labelled conjugates as detection reagents.

A second aspect of the invention is an antibody raised against any of the previously described immunogens, the antibody able to bind to an epitope of a molecule comprising the following structure (Structure 1), in which X can be H or $CH_3$

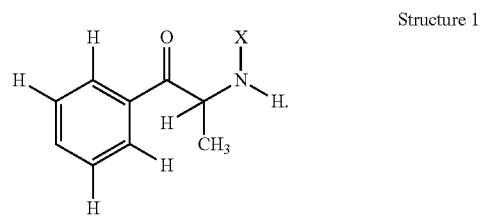

Structure 1

Explicit hydrogen atoms in the above structure imply that the atoms to which these explicit hydrogen atoms are attached may not be substituted by other atoms i.e. the antibody raised by the immunogens of the invention binds to an epitope of molecules comprising the above sub-structure (where X=H or $CH_3$) which includes molecules substituted at the para position of the phenyl ring (para to the propionyl moiety). Substituents at the para position may be any substituent that results in a molecule that falls within the scope of the invention, that is, results in a molecule that is classified as a cathinone-based stimulant. For example, without limiting the invention thereto, substituents at the para position may be selected from H, $CH_3$, —O—$CH_3$ or F, or any other suitable moiety. When X is H and H is present at the para position of the phenyl ring, Structure 1 is cathinone. When X is $CH_3$ and H is present at the para position of the phenyl ring, Structure 1 is 2-methylamino-1-phenylpropan-1-one (methcathinone). When X is $CH_3$ and $CH_3$ is present at the para position of the phenyl ring, Structure 1 is mephedrone (4-methylmethcathinone). When X is $CH_3$ and —O—$CH_3$ is present at the para position of the phenyl ring, Structure 1 is 4-methoxymethcathinone (para-methoxycathinone, methedrone). When X is $CH_3$ and F is present at the para position of the phenyl ring, Structure 1 is 4-fluoromethcathinone (flephedrone).

Thus, Structure 1 may be represented by Structure 2:

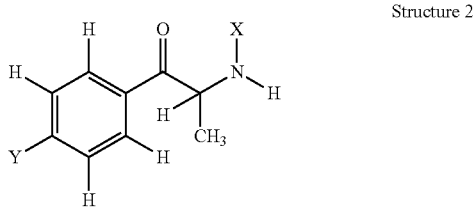

Structure 2 in which Y may be any substituent that results in a molecule that falls within the scope of the invention, that is, results in a molecule that is classified as a cathinone-based stimulant. For example, without limiting the invention thereto, Y may be selected from H, $CH_3$, —O—$CH_3$— or F, or any other suitable moiety. When X is H and Y is H, Structure 2 is cathinone. When X is $CH_3$ and Y is H, Structure 2 is 2-methylamino-1-phenylpropan-1-one (methcathinone). When X is $CH_3$ and Y is $CH_3$, Structure 2 is mephedrone (4-methylmethcathinone). When X is $CH_3$ and Y is —O—$CH_3$—, Structure 2 is 4-methoxymethcathinone (para-methoxycathinone, methedrone). When X is $CH_3$ and Y is F, Structure 1 is 4-fluoromethcathinone (flephedrone).

Preferably the antibody is specific to an epitope of mephedrone and possesses cross-reactivity of greater than 10%, preferably greater than 15% to an epitope of each of cathinone and methcathinone. Thus, the antibody has cross-reactivity to both cathinone and methcathinone that is greater than 10%, preferably greater than 15%.

The antibodies of the invention also bind to mephedrone metabolites (FIG. 2).

When in used in reference to an antibody, the word specific in the context of the current invention refers to the analyte that is preferably bound by the antibody, as gauged by a suitable metric such as the cross-reactivity i.e. the analyte with the greatest cross-reactivity is the antibody specific analyte and is generally given a value of 100%, with all other analytes accorded a value relative to this. The antibody can either be a polyclonal or monoclonal antibody (the monoclonal antibody being derived from the polyclonal antibody using well-known methods); if the polyclonal antibody possesses the required specificity and sensitivity and is produced in adequate quantities, development of a monoclonal antibody is unnecessary.

A further aspect of the invention is a method of detecting or determining a molecule or molecules comprising Structure 1 in an in vitro sample taken from a patient, the method comprising contacting the sample with an antibody of the invention and a conjugate, measuring the conjugate and deducing from a calibrator, the presence of or amount of the molecule or molecules comprising Structure 1. A preferred embodiment is detecting or determining mephedrone, methcathinone and cathinone in an in vitro sample taken from a patient, the method comprising contacting the sample with an antibody of the invention and a conjugate, measuring the conjugate and deducing from a calibrator, the presence of or amount of one or more of mephedrone, methcathinone and cathinone. Mephedrone is especially preferred as a target of the method. Metabolites of mephedrone can also be detected and determined using the method. By "detecting" is meant qualitatively analyzing for the presence or absence of a substance. By "determining" is meant quantitatively analyzing for the amount of a substance.

Another aspect of the invention is a kit for detecting or determining a molecule or molecules of Structure 1 comprising an antibody of the invention. Preferably the kit is used to detect or determine one or more of mephedrone, methcathinone and cathinone, most preferably mephedrone. The kit may also be used to detect metabolites of mephedrone. The kit may further comprise conjugate(s) and/or calibrator(s) and instructions for use of the kit components.

For the purposes of the invention, the patient sample to be used for in vitro analysis can be hair or a peripheral biological fluid but is preferably serum, plasma, or urine.

The conjugates of the method are made up of haptens attached to labelling agents. The haptens of the conjugates are molecules that can bind to the antibodies of the method. The use of haptens, conjugates and antibodies in the context of immunoassays is well known in the art. The labelling agent of the conjugates is selected from an enzyme, a luminescent substance, a radioactive substance, or a mixture thereof. Preferably, the labelling agent is an enzyme, preferably a peroxidase, most preferably horseradish peroxidase (HRP). Alternatively, or additionally, the luminescent substance may be a bioluminescent, chemiluminescent or fluorescent material.

Methods And Results
Preparation of Haptens, Immunogens And Conjugates

Although haptens provide defined structural epitopes, they are not in themselves immunogenic and therefore need to be conjugated to carrier materials, which will elicit an immunogenic response when administered to a host animal. Appropriate carrier materials commonly contain poly(amino acid) segments and include polypeptides, proteins and protein fragments. Illustrative examples of useful carrier materials are bovine serum albumin (BSA), egg ovalbumin, bovine gamma globulin, bovine thyroglobulin (BTG), keyhole limpet haemocyanin (KLH) etc. Alternatively, synthetic poly(amino acids) having a sufficient number of available amino groups, such as lysine, may be employed, as may other synthetic or natural polymeric materials bearing reactive functional groups. Also, carbohydrates, yeasts or polysaccharides may be conjugated to the hapten to produce an immunogen. The haptens can also be coupled to a detectable labelling agent such as an enzyme (for example, horseradish peroxidase), a substance having fluorescent properties or a radioactive label for the preparation of conjugates (or detection reagents) for use in the immunoassays. The fluorescent substance may be, for example, a monovalent residue of fluorescein or a derivative thereof. Immunogen formation can proceed by various synthetic routes. Immunogen formation for the invention described herein involves conventional conjugation chemistry. In order to confirm that adequate conjugation of hapten to carrier material has been achieved, prior to immunisation, each immunogen is evaluated using matrix-assisted UV laser desorption/ionisation time-of-flight mass spectroscopy (MALDI-TOF MS).

General Procedure for MALDI-TOF Analysis of Immunogens

MALDI-TOF mass spectrometry was performed using a Voyager STR Biospectrometry Research Station laser-desorption mass spectrometer coupled with delayed extraction. An aliquot of each sample to be analysed was diluted in 0.1% aqueous trifluoroacetic acid (TFA) to create 1 mg/ml sample solutions. Aliquots (1 µl) were analysed using a matrix of Sinapinic acid and bovine serum albumin (Fluka) was used as an external calibrant.

Preparation of Antisera

In order to generate polyclonal antisera, an immunogen of the present invention is mixed with Freund's adjuvant and the mixture is injected into a host animal, such as rabbit, sheep, mouse, guinea pig or horse. Sheep are the preferred host animal. Further injections (boosts) are made and serum is sampled for evaluation of the antibody titre. When the optimal titre has been attained, the host animal is bled to yield a suitable volume of specific antiserum. The degree of antibody purification required depends on the intended application. For many purposes, there is no requirement for purification, however, in other cases, such as where the antibody is to be immobilised on a solid support, purification steps can be taken to remove undesired material and eliminate non-specific binding.

Immunoassay Development

The process of developing an immunoassay is well known to the person skilled in the art. Briefly, for a competitive immunoassay in which the target analyte is a non-immunogenic molecule such as a hapten, the following process is conducted: antibodies are produced by immunising an animal, preferably a mammalian animal, by repeated administration of an immunogen. The serum from the immunised animal is collected when the antibody titre is sufficiently high. A conjugate is added to a sample containing the target analyte and the raised antibodies, and the conjugate and analyte compete for binding to the antibodies. The process may comprise fixing said serum antibodies to a backing substrate such as a polystyrene solid support or a biochip. The antibodies can be polyclonal or monoclonal, monoclonal antibodies being obtainable from polyclonal sera using standard techniques. The signal emitted in the immunoassay is proportionate to the amount of conjugate bound to the antibodies which in turn is inversely proportionate to the analyte concentration. The signal can be detected or quantified by comparison with a calibrator.

EXAMPLE 1

Synthesis of Mephedrone (FIG. 1)

i) α-bromo-4-methylpropiophenone

4-Methylpropiophenone (30 g, 0.202 mol) in acetic acid (100 ml) was added to a solution of Bromine (34 g, 1.05 eq) in acetic acid (100 ml) dropwise. The mixture was stirred at RT for 4 h. The acetic acid was removed in vacuo. To the residue was added water (100 ml) and extracted with dichloromethane (3×200 ml). Extracts were combined and washed with sat. sodium bicarbonate solution (200 ml), dried over sodium sulphate, filtered and evaporated to dryness. The crude was purified by column chromatography (silica gel: 20% ethyl acetate in hexane) to give the title compound (43.9 g, 95%) as a yellow oil.

ii) Mephedrone hydrochloride

To α-bromo-4-methylpropiophenone (45.2 g, 0.199 mol) in chloroform (500 ml) was added 40% methylamine in water (44.8 ml, 3 eq). The mixture was washed with water (3×200 ml), dried over sodium sulphate and evaporated to dryness. The crude was dissolved in ether (200 ml) and 2M HCl in ether (100 ml) was added and mixture was stirred at RT for 1 hr, in which a white solid formed. This was recovered by filtration to give title compound (17.3 g, 41%) as a white solid.

EXAMPLE 2

Synthesis of 4-(2-methylaminopropionyl)phenoxyacetic acid (Hapten 1)

4-(2-bromopropionyl)phenoxyacetic acid (5 g, 17.5 mmol) in chloroform (50 ml) was stirred vigorously at 35-40° C. and a solution of 40% methylamine in water (4.05 ml, 52 mmol) was added dropwise over 30 mins. Stirring was continued at this temperature for a further 1.5 h after addition. The mixture was evaporated to dryness and the crude residue was purified by column chromatography (silica gel: 10% methanol in chloroform) to give the title product (2.7 g, 65%) as a white foam.

EXAMPLE 3

Synthesis of Hapten1-HRP

EDC hydrochloride (10 mg) was dissolved in water (0.6 ml) and added to a solution of HRP (20 mg) in water (1 ml). The resulting solution was added to a solution of Hapten 1 (2 mg) in DMF (0.2 ml). The resulting solution was added to Sulfo-NHS (5 mg), and the mixture incubated in the dark at 37° C. 16-20 hours, with agitation. Excess hapten was removed with double PD-10 columns (Pharmacia) in series, pre-equilibrated with PBS (pH 7.2) and the Hapten 1-HRP conjugate dialysed overnight against 10 L of PBS (pH 7.2) at 4° C.

EXAMPLE 4

Conjugation of Hapten 1 To BSA (Immunogen 1)

To a solution of the Hapten 1 (34.8 mg, 0.146 mmol) in 1 ml of anhydrous DMF was added N-hydroxysuccinamide (18.4 mg, 0.16 mmol) and N,N-dicyclohexylcarbodimide (33 mg, 0.43 mmol) and the mixture was stirred at room temperature overnight. The white precipitate of urea formed was filtered off and the filtrate was added dropwise to a solution of BSA (150 mg) in 12 ml of 0.1M sodium bicarbonate, pH 8.5. The mixture was then stirred overnight at room temperature. The solution was dialysed against PBS (10 L) for 24 hours. By MALDI-TOF, a major signal was present in immunogen which indicates an average protonated mass at mz 68,535 The data suggests that an average of 9 molecules of hapten have been conjugated per molecule of BSA.

EXAMPLE 5

Conjugation of Hapten-1 To BTG (Immunogen 2)

To a solution of the Hapten 1 (34.8 mg, 0.146 mmol) in 1 ml of anhydrous DMF was added N-hydroxysuccinamide (18.4 mg, 0.16 mmol) and N,N-dicyclohexylcarbodimide (33 mg, 0.43 mmol) and the mixture was stirred at room temperature overnight. The white precipitate of urea formed was filtered off and the filtrate was added dropwise to a solution of BTG (150 mg) in 12 ml of 0.1M sodium bicarbonate, pH 8.5. The mixture was then stirred overnight at room temperature. The solution was dialysed against PBS (10 L) for 24 hours.

EXAMPLE 6

Development of ELISAs For Mephedrone

Hapten 1 was conjugated to bovine serum albumin (BSA). The resulting immunogen (Immunogen 1) was administered to adult sheep on a monthly basis to provide target-specific polyclonal antisera. IgG was extracted from the antisera via caprylic acid/ammonium sulphate precipitation of immunoglobulin. Microtitre plates (Thermo Scientific, 468667) were coated with antibody (125 μl) in coating buffer (10 mM Tris pH 8.5) at 37° C. for 2 hours. The plates were then washed 4 times over 10 minutes with working strength TBST. 50 μl of sample/standard (Methcathinone, Sigma M-5037; Cathinone, Sigma C-3196 and Mephedrone, Randox LK973) was added to the appropriate wells in triplicate, followed by 75 μl of Hapten 1-HRP conjugate and incubated at 25° C. for 1 hour. The plates were then washed and 125 μl of TMB (Randox, 4380-15) was added to each well and left at room temperature for 20 mins in the dark. The reaction was stopped using 125 μl of 0.2M sulphuric acid. The absorbances were read at 450 nm with an ELISA microplate reader (BIO-TEK Instruments, Elx800) and the means calculated.

Results

Competitive immunoassay results at different antibody and conjugate concentrations show the raised antibody binds to mephedrone, methcathinone and cathinone (Table 1).

TABLE 1

ELISA results confirming binding of raised antibody to mephedrone and closely related compounds.

| Conjugate | Std Used For Screening | ELISA Results | | | | |
|---|---|---|---|---|---|---|
| | | Antibody dilution | Conjugate dilution | Zero Absorb. | Standard Absorb. | % Drop |
| Hapten 1-HRP | Methcathinone 100 ng/ml | 5 ug/ml | 1/4K | 1.961 | 0.205 | 89.5% |
| | Cathinone 100 ng/ml | | | 1.961 | 1.600 | 18.4% |
| | Mephedrone 100 ng/ml | | | 1.961 | 0.120 | 93.9% |
| Hapten 1-HRP | Methcathinone 100 ng/ml | 1.25 ug/ml | 1/8K | 1.986 | 0.169 | 91.5% |
| | Cathinone 100 ng/ml | | | 1.986 | 1.515 | 23.7% |
| | Mephedrone 100 ng/ml | | | 1.986 | 0.087 | 95.6% |

The invention claimed is:

1. A method of detecting or determining at least one molecule of Structure 1

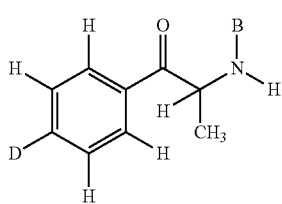

Structure 1 wherein B is selected from the group consisting of H and $CH_3$, and D is selected from the group consisting of H, $CH_3$, —O—$CH_3$ and F, in an in vitro sample taken from a patient, the method comprising
a) contacting the sample with an antibody and a conjugate, the antibody having a cross-reactivity of 100% to mephedrone, and having a cross reactivity of greater than 10% to an epitope of each of cathinone and methcathinone, the antibody being raised against an immunogen of the structure

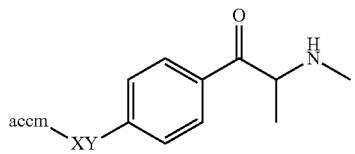

wherein,
accm is an antigenicity conferring carrier material selected from the group consisting of bovine serum albumin (BSA), egg ovalbumin, bovine gamma globulin, bovine thyroglobulin (BTG), and keyhole limpet haemocyanin (KLH);
X is either carbonyl or amino;
Y is —Z—(A)$_n$— in which Z is a $C_{1-5}$, substituted or unsubstituted straight chain alkylene or arylene moiety,
A is O, NH, S, ester, thioester, or amide, and
n=0 or 1 wherein, when A is present, it is linked to the phenyl ring;
b) measuring the conjugate; and
c) deducing from a calibrator, the presence of or amount of the at least one molecule of Structure 1.

2. The method of claim 1 in which the antibody has a cross-reactivity of greater than 15% to an epitope of each of cathinone and methcathinone.

3. The method of claim 1 in which the at least one molecule of Structure 1 is selected from at least one of mephedrone, methcathinone and cathinone.

4. The method of claim 3 in which the antibody has a cross-reactivity of greater than 15% to an epitope of each of cathinone and methcathinone.

* * * * *